United States Patent [19]

Collins

[11] Patent Number: 5,102,669
[45] Date of Patent: Apr. 7, 1992

[54] METHOD OF PRODUCING REMEDIES AND PRODUCTS OF THE METHOD

[76] Inventor: Robert A. Collins, 22 6th Ave. NE., Waukon, Iowa 52172

[21] Appl. No.: 318,069

[22] Filed: Feb. 21, 1989

Related U.S. Application Data

[63] Continuation-in-part of Ser. No. 86,539, Aug. 18, 1987, abandoned, which is a continuation-in-part of Ser. No. 609,277, May 11, 1984, abandoned, which is a continuation-in-part of Ser. No. 528,881, Sep. 2, 1983, abandoned.

[51] Int. Cl.⁵ .............................................. A61K 35/20
[52] U.S. Cl. ................... 424/535; 424/85.8; 424/86; 424/87
[58] Field of Search ............... 424/85, 87, 95, 105, 424/535, 85.8, 86

[56] References Cited

U.S. PATENT DOCUMENTS 3,376,198  4/1968  Petersen et al. .................. 424/85
3,553,317  1/1971  Michaelson et al. ............... 424/87

OTHER PUBLICATIONS

Kabat–Structural Concepts in Immunology and Immunochemistry (1968) p. 191.
Ziv et al.–Chem. Abst., vol. 81 (1974) p. 72463y.
Mol et al.–Chem. Abst., vol. 73 (1970) pp. 119, 351n.

*Primary Examiner*—Sam Rosen
*Attorney, Agent, or Firm*—Ira Milton Jones

[57] ABSTRACT

A method of converting allergenic substances which may have medicinal value into a new, safe and effective non-toxic and novel product having utility as a homeopathic remedy. This invention contemplates converting toxic substances into useful medicaments by a process involving the mammary glands of animals.

12 Claims, 1 Drawing Sheet

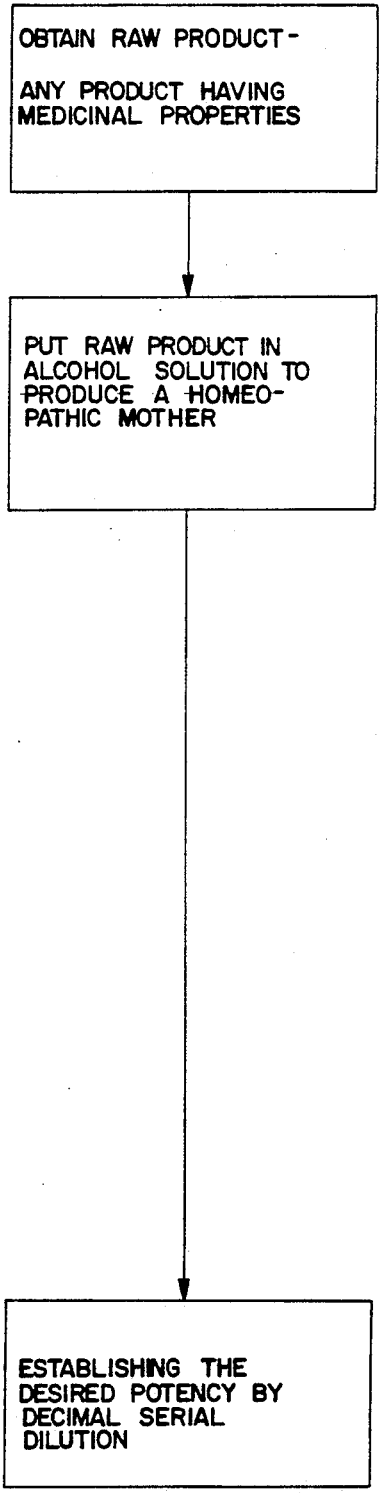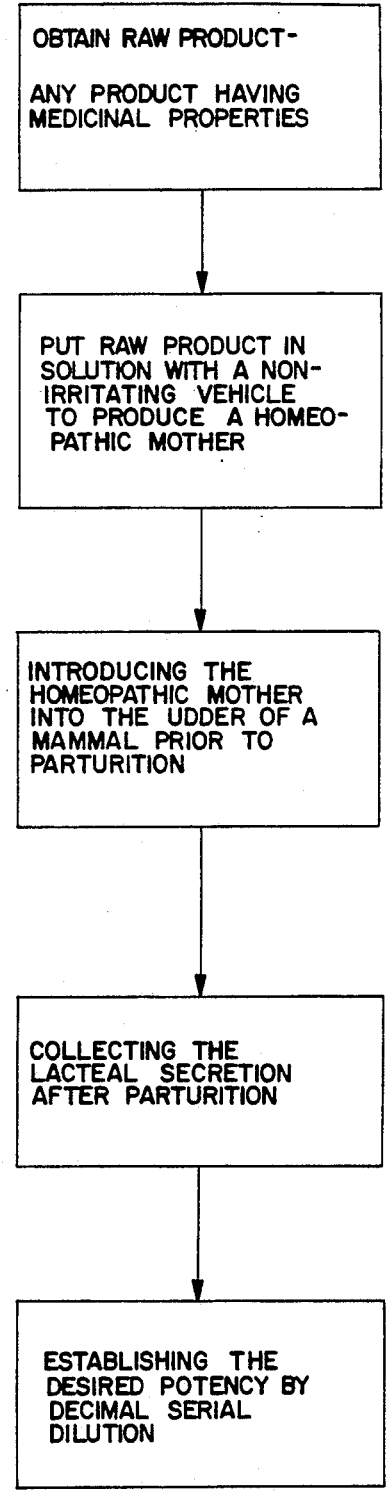

METHOD OF PRODUCING REMEDIES AND PRODUCTS OF THE METHOD

Webster's 3rd International Dictionary defines homeopathy at page 1033, as follows:

"a system of medical practice that treats a disease by the administration of minute doses of a remedy that would in healthy persons produce symptoms of the disease treated."

In the known art of producing homeopathic remedies and in accordance with the principles, methods and terminology described in the Homeopathic Pharmacopoeia of the United State, Eighth Edition 1979; Supplement A-1982 and Compendium of Homeotherapeutics 1974, a raw product is placed either in solution of mixed with lactose to provide a starting solution or mixture known and hereinafter referred to as a mother. The starting solution or mixture is thereafter attenuated in the case of liquids or triturated in the case of insoluble substances to produce a product having homeopathic characteristics which are the same as those of the raw product used in the production of the mother. It should be noted that attenuation or trituration are the terms now used to describe the process of potentizing a substance by dilution and succession.

While this known method can produce a homeopathic remedy that is useful in many instances, there is a definite danger associated with the prior art method when the raw material used in the production of the mother is either a nosode originating from a microorganism, a material resulting from the disease process, a toxin of natural origin, or a toxic chemical or metal. This is especially true in the event of use when the remedy is not needed, since the continued use of the homeopathic remedy past that point of time when the symptoms of the condition being treated have disappeared, can cause those same symptoms to reappear.

Petersen et al, U.S. Pat. No. 3,376,198, Method of Producing Antibodies in Milk, is a related patent. The Petersen et al patent shows use of anti-genetic raw material for use in a non-pathogenic condition. As an example, it specified that the "antigen was dead *salmonella pullorum*." The Petersen et al patent does not use the first mother of a toxic or pathogenic raw material for infusion into the udder of an ungulate and therein converting the first mother into a second mother having the same homeopathic characteristics as the raw material used in the first mother without any of the toxic or pathogenic characteristics that were present in the raw material used in the production of the first mother.

The Petersen et al patent uses the production of antibodies primary for use in the prevention of disease. Hence, Petersen et al could be said to produce a product which is similar to and acts like a vaccine for protection against disease. In this respect, it should be noted that throughout their specification Petersen et al refer to the "protection principle of their invention." Petersen et al thus has, as a primary concern, the production of a specific antibody to antigens for the stimulation in the treated animal of such antibodies or "protective agent" for a new approach to the prevention of disease in animals.

Petersen et al does not teach the use of any antigens such as those either toxic or pathogenic properties whereas the applicant's invention involves the production of a first mother from any selected raw material, even those having toxic or pathogenic characteristics.

Michaelson et al U.S. Pat. No. 3,553,317, IGA Antibody from Lacteal Fluids, is also similar, but is not concerned with the production of homeopathic products by means of a process such as set forth in the claims of the application. Michaelson et al has an objective, the production of a product which he identifies as lactimunin having a molecular weight of 40,000–100,000. He explains that lactimunin is a new antibody. The product produced by the applicant is produced by a different process and is not an antibody, and moreover its molecular weight is less than 2000.

The Michaelson et al patent does not show the production of a first mother using raw material having either a toxic or a non-toxic or a pathogenic property, nor infusion of the first mother into the udder of an ungulate to therein produce a second mother having the same homeopathic properties as the first mother but none of the toxic or pathogenic properties that had been present in the first mother.

Accordingly, it is not believed that the Michaelson et al patent anticipates the applicant's invention.

By definition, the applicant's final produce is a minute fraction of the original crude substance used to produce the first mother. This product has been in effect filtered through the udder of an ungulate in this process of producing a homeopathic-like product. This process and product are not the same as shown in either Petersen et al or Michaelson.

The Petersen and Michaelson patents show processes for producing antibodies. An antibody is a protein substance in the blood or tissue of animals that destroys or weakens a specific bacteria and will agglutinate the specific bacteria in vitro.

The product of the instant invention does not destroy bacteria. The product of the instant invention will not agglutinate specific bacteria in vitro. The action of a product of the instant invention is that it signals the body to expel the specific bacteria which is the crude product used to produce the first mother. It may also interfere with the colonization of a specific bacteria.

Accordingly, it is not the same process or product as set forth in the Petersen or Michaelson patents. Accordingly, these patents are not believed to anticipate the applicant's invention.

In contrast, it is an object of this invention to provide a method of producing a medicinal product having homeopathic characteristics, which method involves the production of a first mother having either toxic or non-toxic properties, and which method is characterized by utilization of said mother to produce a new or second mother which has the same homeopathic characteristics minus any toxic properties present in the first mother.

More specifically, it is a purpose of the invention to produce a homeopathic remedy which involves production of a first mother into the mammary gland of a mammal for conversion therein to a second mother having the same homeopathic characteristics as the raw material used in the production of the first mother, but without any harmful toxic properties that may have been present in the raw material used in the production of the first mother.

It is a further object of this invention to produce an entirely safe homeopathic remedy from raw products that include, but are not limited to, the following: chemical products of natural or synthetic origin, animal substances, allergens such as molds, pollens, house dust, fungus, hair and danger, toxins, parasites and microorganisms such as bacteria and virus, and sperm.

It is still another object of this invention to infuse a homeopathic substance into the udder of a mammal, to therein effectively remove the substance itself while transferring its homeopathic characteristics to the lacteal secretion.

With these observations and objectives in mind, the manner in which the invention achieves its purpose will be appreciated from the following description and the accompanying drawing, which exemplifies the invention, it being understood that changes may be made in the precise method of practicing the invention without departing from the essentials of the invention set forth in the appended claims.

The accompanying drawing diagrammatically illustrates a comparison between the old and new methods of producing the homeopathic remedy of this invention, in which:

FIG. 1 is a block diagram illustrating the known method of producing products having homeopathic characteristics; and FIG. 2 is a similar block diagram illustrating the method of this invention.

The main distinctions are of substantial importance and reside in:

(1) the raw material for production of the desired homeopathic remedy can be one which is either toxic or non-toxic in nature; and (2) the vehicle use in producing the homeopathic mother should be a non-irritant, as distinguished from the conventional vehicle, preferably whey, distilled water or a physiological saline solution.

In a more specific sense, the first step of obtaining the raw material in the practice of the invention may be substantially the same as the first step in producing a homeopathic remedy as outlined in the Homeopathic Pharmacopoeia of the United States, Eighth Edition 1979 and Supplement A-1982. The raw material may be any chemical product of natural or synthetic origin, biological preparations in the wider sense, and any substance which may be considered to have medicinal value such as—but not limited to—all the substances listed in the Homeopathic Pharmacopoeia of the United States, Eighth Edition 1979.

However, the raw product or medicinal substance chosen to produce the homeopathic remedy in accordance with this invention can be either of a toxic or non-toxic nature, and it is then put into suspension according to the procedure laid out in the Homeopathic Pharmacopoeia of the United States, Eighth Edition 1979 and Supplement A-1982, with the exception of the solvent. The ethyl alcohol prescribed in the Homeopathic Pharmacopoeia of the United States Eighth Edition 1979 is such an irritant and, according to this invention is replaced with a non-irritating vehicle. I have found physiological saline, distilled water and/or a purified whey in which the solids are over 80% (eighty percent) lactose to be good non-irritating substitutes for alcohol. Such materials are available on the market.

The purified high lactose whey can be produced using a high speed continuous centrifuge that will remove all particles over 0.4 micron size. This high lactose whey is preferably then sterilized by passing it through a 0.2 micron sterilizing filter.

Any mammal may be used in the practice of this invention. Cows and goats were used, but cows were found to be the most practical.

Any method can be used to introduce the homeopathic mother (the first mother) into the cistern of the udder. This can be done either before or after parturition. Two methods have been used in the practice of this invention: infusing the first mother into the cistern through the orifice of the teat canal, using a sterile 10 cc syringe equipped with a blunt cannula; or, alternatively, injecting the side of the udder using a 10 cc sterile syringe equipped with a needle of suitable length. The infusion method has been found to be more feasible for repeated doses but requires more care to maintain sterility of equipment.

A satisfactory dose of the first mother inserted into the udder of each cow, or other mammal, has been found to comprise 10 cc per quarter of a sterile suspension of a specific allergenic extract having about 3260 P.N.U. (Protein Nitrogen Units) per cc. Allergenic extracts are a commercially available product and comprise the allergens mentioned hereinbefore.

Regardless of which allergens are used in the production of the first mother, a 10 cc dose of the solution of the first mother, prepared as outlined above, is preferably infused into each quarter of a cow, using asceptic techniques, two or three times at 7 to 12 day intervals prior to parturition. Lactating cows may be used but the use of dry cows has been found to be less upsetting to the cow.

When dry cows are infused, the colostrum and first milk as it comes from the cow after parturition is saved and is used as a second mother for the preparation of a homeopathic product by accepted methods of attenuation.

This invention will produce a homeopathic product that is effective in overcoming a disease that in many instances a regular homeopathic product, made from the same starting material, was found to be ineffective.

In the practice of producing homeopathic remedies, a life-death challenge test is not used. With the method of the instant invention of utilizing the cow to produce a second mother for the production of a homeopathic product, a life-death challenge test is feasible.

The following experiment was carried out to establish the potency of a product produced by the method of this invention. Experimental procedure and results of challenge follow.

A smooth colony of a pathogenic *pseudomonas aerogenosa* cultured from a veterinary posting specimens taken from diseased calves, was asceptically transferred to media and processed into a vaccine by methods known in the art. The vaccine was heat-killed, corrected to a density of McFarland 5, and bottled in 40 ml sterile serum bottles, capped with a sterile rubber stopper. A second calf Holstein heifer was health-checked by a veterinarian. This cow was infused with 5 ml of the above vaccine, intermammary, three times at weekly intervals just prior to parturition.

When the cow calved, one gallon of colostrum was saved in a gallon jug market "A" and refrigerated, and one gallon of milk was saved in a gallon jug marked "C" and refrigerated. One ml colostrum from jug "A" was vigorously mixed with 9 ml sterile distilled water in a 20 ml test tube and capped with a sterile rubber stopper. This process was carried out in a sterile room under a Hepa filter. 1 ml of this dilution was mixed with 9 ml sterile distilled water and vigorously mixed by shaking and vortexing the fluid.

1 ml of this 2nd serial dilution was diluted with 9 ml sterile distilled water and vigorously mixed as above, in a 20 ml test tube. This 3rd serial dilution was then bottled in sterile 20 ml serum bottles, capped with a sterile rubber stopper and sealed with an aluminum crimped seal. This was marked A-3x. 1 ml colostrum from the jug marked "A" was serial diluted in the same manner described above for six serial dilutions. The sixth dilution was sterile bottled in 20 ml serum bottles using the technique described above. This bottle was marked A-6x.

1 ml milk from the jug marked "C" was serial diluted with 9 ml water, vigorously mixed and vortexed in a 20 ml test tube. This process was carried out to 3 serial dilution in the same manner as above. The product of the 3rd dilution was then sterile bottled in 20 ml serum bottles, capped with a sterile rubber stopper and sealed with an aluminum crimped seal. This bottle was marked C-3x.

1 ml milk from the jug marked "C" was diluted with 9 ml sterile distilled water in a 20 ml test tube, stoppered and vigorously mixed by shaking and vortexing. This process was carried out for a total of six serial dilutions. The product of the sixth serial dilution was then bottled in 20 ml sterile serum bottles, capped and sealed as above. This bottle was marked C-6x.

The four products marked A-3x, A-6x, C-3x and C-6x were then tested on mice previously injected I.P. with a lethal challenge of pathogenic *pseudomonas aurogenosa* at the rate of $25 \times 10^6$ per ml. Results were as follows:

From the description thus far, it will be noted that the practice of my invention is a two-phase operation. The first phase involved the production of a homeopathic mother to be used in the production of a second mother.

An example of the method I have employed in producing the first mother consisted in the use of 100 cc of specific *pseudomonas aurogenosa* vaccine prepared by methods well known in the art, inactivated by heat and corrected to a concentration of McFarland 5 density. McFarland 5 density is a term used to designate the potency of a vaccine and is commonly used by persons skilled in the art of preparing vaccines. McFarland density is a scale of densities and McFarland 5 is a density of $1500 \times 10^6$ bacterial ml.

Using sterile techniques, 60 cc of the above pseudomonas aurogenosa vaccine was diluted with 60 cc of sterile whey.

The first mother was sterile bottled in these 40 cc vials equipped with sterile rubber sleeve stoppers and stored under refrigeration for later use in the production of a second mother. The 40 cc vial size was employed for convenience in later infusion into the udder of the cow, 10 cc per quarter.

Another example of producing a first mother for use in the second phase of my invention involves the use of an insoluble metal as the raw medicinal product. Aluminum is such an insoluble material. In this case I added one gram of water-soluble aluminum orotate to 99 cc of distilled water to produce a solution. At this point 20 cc of the above solution was added to 20 cc of purified whey that had been previously filtered through a 0.2 micron filter to produce one animal infusion in the case

| Type of raw product used to produce 2nd mother | TREATMENT Dosage: 1 ml | PSEUDOMONAS CHALLENGE | RESULTS | | |
|---|---|---|---|---|---|
| | | | Alive | Sick | Dead |
| | | TEST 1 | | | |
| NON USED** | WATER | $25 \times 10^6$ | 1 | 0 | 3 |
| NON USED | 2 mg eq. 390* | " | 4 | 0 | 0 |
| COLOSTRUM | A 3x | " | 2 | 0 | 2 |
| COLOSTRUM | A 6x | " | 3 | 0 | 1 |
| MILK | C 3x | " | 1 | 0 | 3 |
| MILK | C 6x | " | 3 | 0 | 1 |
| NON USED** | Water (one mouse) | 0 | 1 | 0 | 0 |
| | | TEST 2 | | | |
| NON USED** | WATER | $25 \times 10^6$ | 1 | 0 | 3 |
| NON USED | 2 mg eq. 390* | " | 4 | 0 | 0 |
| COLOSTRUM | 1 cc A 3x | " | 3 | 0 | 1 |
| COLOSTRUM | .5 cc A 3x | " | 4 | 0 | 0 |
| COLOSTRUM | .25 cc A 3x | " | 4 | 0 | 0 |
| MILK | 1 cc C 3x | " | 3 | 0 | 1 |
| MILK | .5 cc C 3x | " | 4 | 0 | 0 |
| MILK | .25 cc C 3x | " | 3 | 0 | 1 |
| NON USED** | WATER | 0 | 4 | 0 | 0 |

4 mice per group
*390 is our positive control
A Colostrum used as a raw material to produce the second mother
C Milk used as raw material to produce the second mother
**Control
Tests conducted at Derse Schroeder Laboratories Madison, Wisconsin The first mother may be either a Class A or a Class L raw medicinal product. These products are defined in the Homeopathic Pharmacopoeia of the United States, pages 54 and 65 respectively, of the Eighth Edition, first Supplement. As therein seen, Class L products are pathogenic or toxic.

The second mother produced in accordance with the method described above, is always a Class A material. This is true even when the first mother used in the production is a Class L or pathogenic substance.

of a cow, or two animal infusions for goats.

This first mother was stored under refrigeration for use in the production of the second mother int he second phase of the invention.

The second phase of this invention involves the production of a second mother possessing the homeopathic characteristics of the first mother. This process may begin with a lactating animal or during its dry period.

An example of the method of producing the second mother involved use of a healthy cow carrying her second or later calf, about one month preparatum. The udder and teats are prepared and treated in the following manner:

(1) Wash with water and soap and rinse with clean water;

(2) Dry with individual paper towels;

(3) Cover test opening (or point of injection if one chooses to go through the side of the udder) with a cotton swab previously soaked in a 70% alcohol solution;

(4) Fill four 10 cc syringes with the previously prepared first mother, using a sterile syringe needle for withdrawal from the bottle;

(5) When introducing the substance into the udder via the teat canal, remove the needle from the syringe and replace with a sterile cannula;

(6) Remove the alcohol swab and inset the blunt cannula into the orifice of the teat and expel the contents into the cistern of the quarter. All must be done in an asceptic manner. If the cannula is accidentally contaminated by touching the side of the teat or the operator's fingers, it should be discarded and replaced with a sterile cannula.

A separate syringe and sterile cannula should be used for each quarter. This procedure should be repeated two or three times at seven to ten day intervals prior to parturition. At parturition, for the production of a high potency product of this invention, a few pounds of the colostrum and milk is saved in well-marked containers and frozen for storage. Prior to freezing the colostrum and milk is filtered through a 0.2 micron filter which filters out large molecules and antibodies. An 0.1 micron filter may be used which will filter out smaller molecules and antibodies. It is not necessary that the milk be filtered as long as some suitable means of separating out the larger molecules is used.

1cc of this colostrum or milk can now be used to produce a second mother by adding 1 cc of the colostrum or milk to 9 cc of water, or water and ethyl alcohol, to produce a 10% (10:1) liquid attenuation which is designated 1X. The best method to get this in solution is with the use of a Vortex mixer.

This serial dilution and succession is repeated, using 1 cc of the previous mixture and 9 cc of distilled water or alcohol until the desired solution is arrived at.

For purposes of the study hereinafter referred to, two products were prepared in accordance with the previously outlined steps of the method of this invention namely:

(1) prepare the first mother using *psuedomonas aerogenosa* vaccine;

(2) infuse the cow with such first mother to produce the second mother;

(3) prepare two test products of potency of 3X (1:1000 dilution) and 6X (1:1,000,000 dilution).

In order to establish the utility of a product produced by the method of my invention described above, a series of challenge and protection tests were conducted using mice to establish the efficacy of this homeopathic product.

First, in the establishment of a lethal dose, it was found that $25 \times 10^6$ organisms of a specific pseudomonas injected I.P. would kill two out of three mice. All mice indicated were challenged with $25 \times 10^6$ specific pseudomonas organisms I.P.

The first test was performed to observe the effect of a 1 cc injected I.P. of a 3x and 6x homeopathic remedy prepared using one gram of colostrum or one gram of milk, to produce the second mother and then serially diluting and succusing 1 cc of the second mother and 9 cc of distilled water to a dilution indicated as either 3x or 6x.

The second test was conducted to indicate the effect of varying the dosage of the homeopathic remedy.

These tests, depicted on the following chart, prove the efficacy of the homeopathic remedy of this invention.

| Type of raw product used to produce 2nd mother | TREATMENT | PSEUDOMONAS CHALLENGE | RESULTS Alive | Sick | Dead |
|---|---|---|---|---|---|
| | | TEST 1 | | | |
| | WATER | $25 \times 10^6$ | 1 | 0 | 3 |
| | 2 mg eq. 390 | " | 4 | 0 | 0 |
| COLOSTRUM | A 3x | " | 2 | 0 | 2 |
| COLOSTRUM | A 6x | " | 3 | 0 | 1 |
| MILK | C 3x | " | 1 | 0 | 3 |
| MILK | C 6x | " | 3 | 0 | 1 |
| | Water (one mouse) | 0 | 1 | 0 | 0 |
| | | TEST 2 | | | |
| | WATER | $25 \times 10^6$ | 1 | 0 | 3 |
| | 2 mg eq. 390 | " | 4 | 0 | 0 |
| COLOSTRUM | 1 cc A 3x | " | 3 | 0 | 1 |
| COLOSTRUM | .5 cc A 3x | " | 4 | 0 | 0 |
| COLOSTRUM | .25 cc A 3x | " | 4 | 0 | 0 |
| MILK | 1 cc C 3x | " | 3 | 0 | 1 |
| MILK | .5 cc C 3x | " | 4 | 0 | 0 |
| MILK | .25 cc C 3x | " | 3 | 0 | 1 |
| | WATER | 0 | 4 | 0 | 0 |

4 mice per group
390 is our positive control for protection of animal
A colostrum used to produce the second mother
C milk used to produce the second mother
Tests conducted at Derse-Schroeder Laboratories, Madison, Wisconsin It is important to note that in accordance with this invention, the introduction of the first mother into the udder of a mammal effects a conversion therein of the raw material into new and different cells which, however, have the same homeopathic characteristics as the raw material used in the production of the first mother.

EXAMPLE 1

One hundred and thirty (130) milk samples were collected from cows (in four herds) that had visible udder congestion and/or abnormal milk. These samples were streaked on EMB and blood agar with azide plates. These prepared plates were then incubated at 37° C. for twenty-four (24) hours, after which screening for pathogens was carried out. From these specimens, a colony of staphylococcus aureus was transferred, via aseptic technique, to media and processed into a vaccine by the methods known in the art, thus producing the first mother. This vaccine was then heat-killed and standardised to a density of McFarland 5, a standard used in the preparation of vaccines. The vaccine was then bottled aseptically in 60 cc serum-type glass vials, capped with sterile rubber stoppers and sealed with aluminum seals. It was marked Staph-I for identification. A code number was also assigned.

For the production of the second mother, a cow 3-4 weeks prepartum was selected. A visible health check was made by a veterinarian, along with a brucella and TB test. Care was taken to see that the teats were clean and dry prior to infusing. Each teat was dried after washing with an individual paper towel. Each teat was then covered with a thin cotton pad soaked in 70% alcohol and left a few minutes.

Four sterile 5 cc syringe equipped with an 18 gauge hypodermic needle was each filled with the vaccine from the bottle marked Staph-1, previously prepared. The hypodermic needles were then disconnected from each syringe and replaced with a sterile plastic canulae. As each canulae was attached, the anulae end of the syringe was stored in an open sterilizing bag for protection. The cow was then infused, through the teat opening, using the prepared syringes.

The infusion was repeated at seven-day intervals for a total of three infusions. Detailed records were maintained, including the cow identification, the vaccine dose, dates and times of infusion, date of calving and the initials of the person doing the work.

Preferably when the cow is calved, the cow was milked and the milk was filtered with a 0.1 micron filter to filter out antibodies. One gallon of this filtered colostrum and early milk was saved in a gallon plastic jug. The jug was tagged, using a waterproof tape, showing the date, vaccine code and the cow number or name. The identification, Staph-1, was also put on the jug, using a permanent magic marker. The jug with the Staph-1 colostrum was frozen for storage.

Three additional pathogens were selected from the above screen, specifically:

1. a α *streptococcus agalactiae* colony
2. a γ *streptococcus agalactiae* colony
3. An *E. Coli* colony.

The same procedure that was used to produce the Staph-1 product, detailed above, was employed to produce a product starting with each of the isolates listed above. Three 2nd-calf Holstein cows, all about one month prepartum, were selected. One for each of the three additional products to be produced. One for the α streptococcus agalactae, one for the α *streptococcus agalactae* and one for the *E. coli*.

As these cows calved, one gallon of colostrum was saved in a plastic jug. The jug was tagged with the code assigned the isolate referenced and the cow number or name. The jug was then frozen for storage. When all three jugs were frozen, they were thawed, along with the jug coded Staph-1 produced earlier.

One ounce was removed from each of the four jugs and put in an 8 oz wide-mouth screw top jar and capped with a metal cap. These four products were thoroughly mixed by shaking and rolling end over end. The jar was coded with each of the four codes used to identify each isolate and each cow used to produce the four individual components of this jar.

From this point on, all work was carried out under a Hepa filter, using aseptic procedures, by gowned and masked technicians, wearing sterile rubber gloves.

One ml of the product in the jaw with the four components was withdrawn using a sterile pipette. This was added to 9 ml sterile distilled water in a 20 ml sterile test tube, stoppered with a sterile rubber stopper. This tenfold dilution was vigorously mixed by shaking and vortexing.

One ml of this first serial dilution was then diluted with 9 ml sterile distilled water and thoroughly blended as above. This process was carried out for six serial dilutions.

The product of the sixth serial dilution was bottled in 50 ml sterile serum type bottles, capped with a sterile rubber cap and sealed with an aluminum seal. Ten 50 cc bottles were then sent to the veterinarian doing the research.

Each month the cows in a herd having high cell counts are listed on the owners DH1A report for treatment. The high cell count cows in the herd were treated with 2-4 cc (ml) doses of the product orally on their feed at twelve-hour intervals, with the following results:

| Cow No. | SCC on March 5 | Treatment | SCC on March 20 |
|---|---|---|---|
| \multicolumn{4}{l}{Problem cows in herd code DM-10} |
| \multicolumn{4}{l}{High Somatic Cell Count (SCC), March 1987} |
| 66 | >1,000,000 | 2-4 5 cc MT on feed | <200,000 |
| 65 | " | " | <200,000 |
| 60 | " | " | >1,000,000 |
| 82 | " | " | >1,000,000 |
| 172 | " | " | 1,000,000 |
| 146 | " | " | <200,000 |
| 69 | " | " | <200,000 |
| 173 | " | " | <200,000 |
| 200 | " | " | <200,000 |
| 136 | " | " | <200,000 |
| 124 | " | " | <200,000 |
| 150 | " | " | <200,000 |

| Cow No. | SCC on June 17 | Treatment | SCC on June 22 |
|---|---|---|---|
| \multicolumn{4}{l}{June 1987} |
| 82 | >1,000,000 | 5 cc MT, 2-4 times 12 hr interval on feed | <200,000 |
| 52 | " | 5 cc MT, 2-4 times 12 hr interval on feed | <200,000 |
| 154 | " | 5 cc MT, 2-4 times 12 hr interval on feed | <200,000 |
| 151 | " | 5 cc MT, 2-4 times 12 hr interval on feed | <200,000 |
| 37 | " | 5 cc MT, 2-4 times 12 hr interval on feed | <600,000 |
| 196 | " | 5 cc MT, 2-4 times 12 hr interval on feed | >1,000,000 |
| 120 | " | 5 cc MT, 2-4 times 12 hr interval on feed | <200,000 |
| 140 | " | 5 cc MT, 2-4 times 12 hr interval on feed | <200,000 |
| 464 | " | 5 cc MT, 2-4 times 12 hr interval on feed | <200,000 |
| 60 | " | 5 cc MT, 2-4 times 12 hr interval on feed | >1,000,000 |

| -continued | | | |
|---|---|---|---|
| 61 | " | 5 cc MT, 2-4 times 12 hr interval on feed | <200,000 |
| 75 | " | 5 cc MT, 2-4 times 12 hr interval on feed | <200,000 |

Note: Only one cow, #60, repeated in the second list in June. The necessity of reducing a high cell count in a dairy herd is essential in selling milk. Herds with cell counts over one and one-half million are prohibited from selling their milk on the market.

EXAMPLE 2

Three of the four jugs of colostrum produced for Example 1 above were removed from the freezer and thawed. 25 ml was transferred from the jug with the Code Staph -1 and put in a 6 oz glass jar. 25 ml was transferred from the jug marked α strep and transferred to the same 6 oz jar. 25 ml of the product in the jug marked γ strep was transferred to the same 6 oz glass jar. A 25 ml pipette was used to make the above transfers.

The 6 oz jar was capped and thoroughly blended by shaking. 1 ml of the product in this 6 oz glass jar was transferred to a 20 ml sterile test tube containing 9 ml sterile distilled water. This transfer was accomplished by the use of a sterile pipette. This test tube was stoppered with a sterile rubber stopper and vigorously mixed by shaking and vortexing.

1 ml of this first 10-fold dilution was aseptically transferred to a second 20 ml sterile test tube containing 9 ml sterile distilled water. This serial dilution was mixed by vigorously shaking and vortexing. This process was carried to the 6th serial dilution.

On the 5th and 6th dilution, all of the product was processed.

The 6th dilution was sterile bottled in 60 cc serum bottles. The label, serial number and code were referenced to the original culture.

Ten 50 ml bottles of this coded product were delivered to the veterinarian. Eighteen (18) cows in five herds, with clinical mastitus were treated with this 6th dilution product. Following are the results:

- RESULTS -

| Cow Identification | Condition | Treatment Amount | Number of Treatments | Hours to Return to Normal |
|---|---|---|---|---|
| #11RN | Clincal | 10 cc IU* | 2 | 36 |
| #33RN | Clincal | 10 cc IU | 2 | 36 |
| #7RN | Clinical | 10 cc IU | 3 | 48 |
| #20JS | Clinical | 10 cc IU | 3 | 48 |
| #38JS | Clinical | 10 cc IU | 2 | 36 |
| #39JS | Clinical | 10 cc IU | 1 | 24 |
| #55JS | Clinical | 10 cc IU | 2 | 60 |
| #57JS | Clinical | 10 cc IU | 1 | 48 |
| #79TH | Clinical | 10 cc IU | 4 | 48 |
| #14TH | Clinical | 10 cc IU | 3 | 48 |
| #23JS | Clinical | 10 cc IU | 2 | 24 |
| #84JS | Clinical | 10 cc IU | 1 | 24 |
| RedJS | Clinical | 10 cc IU | 2 | 36 |
| WhiteJS | Clinical | 10 cc IU | 2 | 24 |
| #180CT | Clinical | 10 cc IU | 3 | Failed |
| #H21CT | Clinical | 10 cc IU | 4 + 3 orally | Failed |
| #R23CT | Clinical | 10 cc IU | 2 | Partial |
| #46JA | Clinical | 10 cc IU | 4 | Failed |

There is a great economic advantage in getting clinical cows back to normal without the use of antibotics. This is due to the milk throwaway required when antibiotics were given a lactating dairy cow.
*Inter udder From the foregoing description together with the accompanying drawing, it will be apparent to those skilled in the art that this invention provides a new and improved process for producing a homeopathic product superior to any heretofore produced.

The invention is defined by the following claims:

I claim:

1. In the process of producing a homeopathic product having a molecular weight of less than 2000, the steps of:
   A. selecting an allergenic raw material having either toxic or non-toxic or pathogenic or non-pathogenic characteristics;
   B. combining such material with a vehicle which is non-irritating to tissue to produce a combination hereinafter referred to as a homeopathic first mother;
   C. introducing a homeopathic mother into a mammal's udder and effecting conversion of the raw product in said combination into a secretion hereinafter referred to as a second mother having the characteristics of a sarcode and the homeopathic characteristics of the first mother, and not depending on antibodies as a remedy;
   D. removing the second mother from the udder and separating out and disposing of larger molecules including antibodies from the second mother which are approximately 0.2 micron and larger; and
   E. serially diluting said second mother to $10^3$ to $10^{30}$.

2. The process of claim 1, wherein said conversion is effected in the udder of an ungulate.

3. The process of claim 1, wherein said combination is introduced into the udder of a cow or goat, to therein effect said conversion of the raw product into a sarcode suitable for use in the production of a homeopathic remedy.

4. The process of claim 3, further characterized by attenuating said resulting carcode to establish the desired potency thereof.

5. The process of claim 1, wherein said combination is introduced prepartum into the udder of a mammal to effect said conversion therein, and
   wherein lacteal secretion is withdrawn from the mammal follow parturition.

6. The process of claim 1, wherein said combination is introduced into the udder of a mammal during lactation to effect said conversion therein, and
   wherein lacteal secretion is subsequently withdrawn from the mammal.

7. The process of producing a homeopathic product which is characterized by:
   A. preparing a first mother from a vaccine that has been inactivated either by heat or chemicals and having a density of McFarland 5, and placing said vaccine in a solution with a vehicle which is non-irritating to tissue;
   B. introducing the first mother in an ungulate's udder and effecting conversion of said first mother into a second mother having the characteristics of a sarcode and the homeopathic characteristics of the first mother, and not depending on antibodies; and
   C. removing the second mother from the udder, filtering out larger molecules including antibodies from the second mother with approximately a 0.1 micron filter and serially diluting said second mother.

8. The process of producing a homeopathic product, characterized by introduction into the udder of a mammal an allergenic homeopathic first mother having either toxic or non-toxic or pathogenic or non-pathogenic characteristics, effecting removal in said udder of all dangerous or harmful constituents from said mother and producing lacteal fluid, withdrawing lacteal fluid from the udder without loss of the desirable homeopathic characteristics of said mother, and not depending on antibodies, separating out and disposing of larger molecules including antibodies from the lacteal fluid which are approximately 0.1 micron and larger, and serially diluting said second mother.

9. The process of claim 8 wherein the initial allergenic substance is an allergen selected from the group consisting of molds, pollens, house dust, fungus, hair, dander, toxins, parasites, microorganisms, bacteria, virus, and sperm.

10. A homeopathic product produced in accordance with the methods as set forth in any one of claims 1 through 8.

11. The process of producing a homeopathic product including the steps of:
   A. selecting an allergenic raw material having either toxic or non-toxic or pathogenic or non-pathogenic characteristics;
   B. creating a solution of such material using a vehicle which is non-irritating to tissue, to produce a homeopathic first mother;
   C. introducing the homeopathic mother into a mammal's udder and effecting conversion of the raw product in said solution into an allergenic a second mother having the characteristics of a sarcode and the homeopathic characteristics of the first mother and not including antibodies;
   D. collecting lacteal secretion;
   E. establishing the desired potency;
   F. filtering out larger molecules including antibodies from lacteal secretion with approximately a 0.1 micron filter;
   G. and serially diluting said second mother.

12. The method of producing a mother for use in the production of a homeopathic product including the steps of:
   A. selecting an allergenic material having either toxic or non-toxic or pathogenic or non-pathogenic characteristics;
   B. creating a solution of such material using a vehicle which is non-irritating to tissue, to produce a homeopathic first mother;
   C. introducing the homeopathic mother into an ungulate's udder and effecting conversion of the raw product in said solution into a second mother having the characteristics of a sarcode and the homeopathic characteristics of the first mother and not including antibodies;
   D. collecting lacteal secretion;
   E. establishing the desired potency;
   F. filtering out larger molecules including antibodies from lacteal secretion with approximately a 0.1 micron filter;
   G. and serially diluting said second mother.

* * * * *